United States Patent

Carlini et al.

[11] Patent Number: 6,062,094
[45] Date of Patent: May 16, 2000

[54] DUST MEASUREMENT SYSTEM FOR GRANULAR MATTER

[75] Inventors: Archimedo M. Carlini; Gary L. McGowan; Mark B. Ogzewalla, all of Winter Haven, Fla.

[73] Assignee: ARR-MAZ Products, L.P., Winter Haven, Fla.

[21] Appl. No.: 09/326,523

[22] Filed: Jun. 4, 1999

[51] Int. Cl.$^7$ .................................................. G01N 1/00
[52] U.S. Cl. .............................................................. 73/866
[58] Field of Search ............................. 73/865.5, 863.21, 73/863.23, 866, 28.01, 28.04; 96/413, 417, FOR 166

[56] References Cited

U.S. PATENT DOCUMENTS

| | | | |
|---|---|---|---|
| 4,079,621 | 3/1978 | Batzar | 73/866 |
| 4,249,655 | 2/1981 | Patureau . | |

OTHER PUBLICATIONS

Tennessee Valley Authority, Dec. 1979. "TVA Procedures for Determining Physical Properties of Fertilizers" Special Report No. S–444 pp. 306 & 307.

Primary Examiner—Robert Raevis
Attorney, Agent, or Firm—Dennis G. LaPointe; Mason & Associates, PA

[57] ABSTRACT

An apparatus for measuring a dust content in a sample of granules includes an elongate vertically oriented generally cylindrical hollow tower with a bottom portion, an intermediate portion and a top portion adapted to detachably engage the intermediate portion. The bottom portion further includes collection means for collecting the granules processed through the tower. Air is recirculated through the apparatus using air recirculation means such as a blower/vacuum device. A series of valves and pressure sensing gauges for regulating and controlling the air flow are installed within the recirculation path. The tower intermediate portion further includes a plurality of horizontally oriented grates, each grate being secured in a predetermined space apart relationship. A filter is used between the top portion and the intermediate portion to trap dust blown from the granules as the granules are dropping through the grates. A method of using the apparatus is also presented for calculating the amount of dust in a sample of granules.

25 Claims, 1 Drawing Sheet

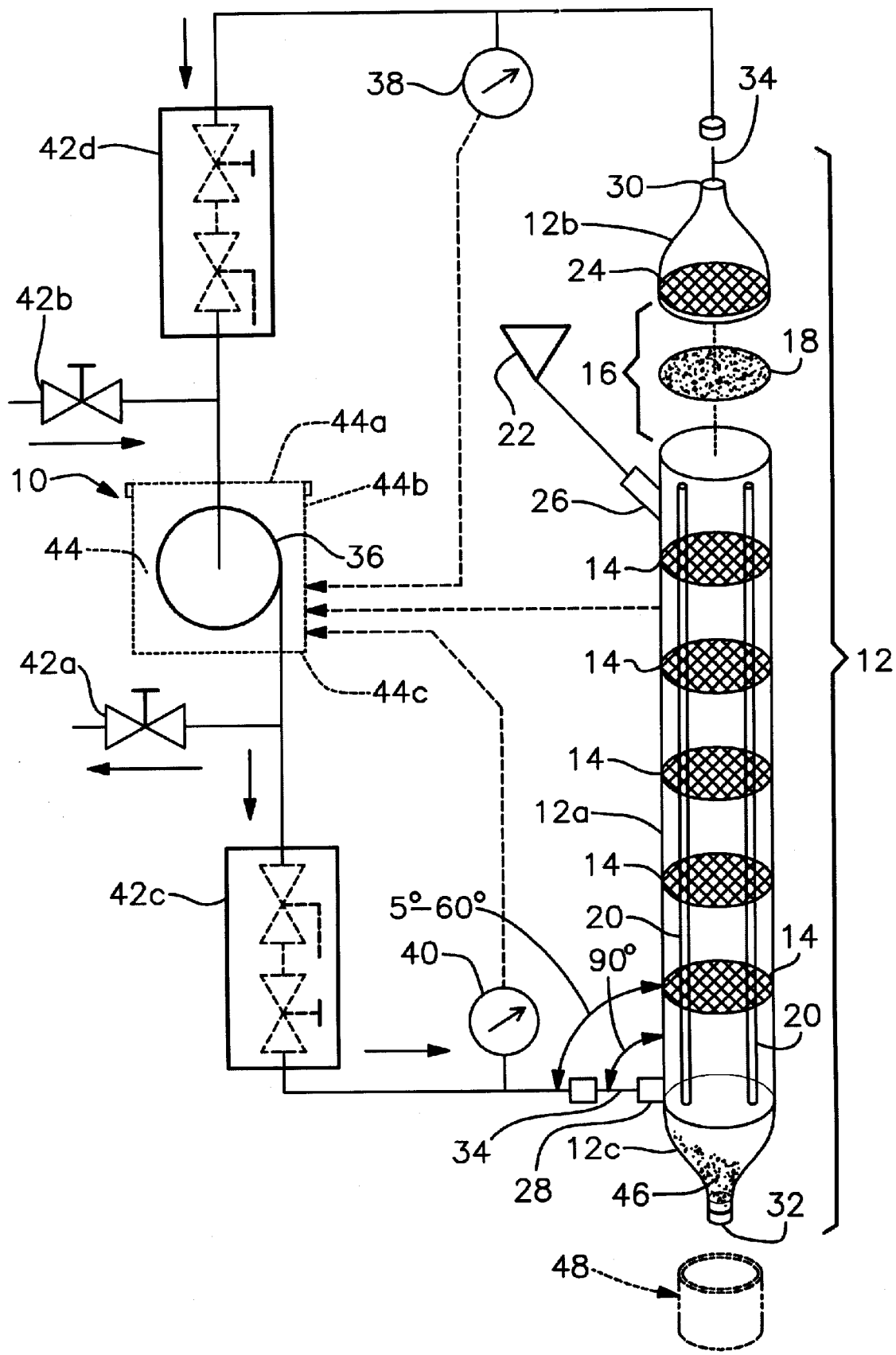

DUST MEASUREMENT SYSTEM FOR GRANULAR MATTER

BACKGROUND OF THE INVENTION

1. Field of the Invention

The invention relates to a dust measurement system and device for measuring dust from granular matter. It relates particularly, to a closed system and device to accurately test and quantify the amount of dust in granular fertilizer at the point of storage and use in the field.

2. Description of Related Art

Methods of measuring the amount of dust in granular fertilizers in laboratories are known in the art. However, the ability to accurately test and quantify the amount of dust in granular fertilizer to evaluate dust control measures in the field is lacking in the fertilizer industry.

Related art for specifically removing dust from granular fertilizer samples includes Reference Manual IFDC-R-1 (International Fertilizer Development Center) entitled "TVA Procedures For Determining Physical Properties Of Fertilizer" describing a Tennessee Valley Authority (TVA) method for laboratory measurement of dust. The apparatus described therein attempts to remove the dust by agitating the fertilizer as it is passed through a series of grates with air blowing in the opposite direction in what may be called a distillation tower. The dust is blown out to the environment and the sample is weighed before and after testing to quantify the amount of dust.

However, the prior art device is used in a lab, generally remote from the worksite, such that a time lag of several days can occur between sample gathering and testing and evaluating the need for further dust control measures. In addition, sample gathering in the field for analysis is, by itself, time intensive, and proper containers are needed to maintain the integrity of the sample during shipping to the lab. Proper transportation to the analysis site has to be arranged including ensuring compliance with transportation and environmental related regulatory requirements. Proper sample labeling and storage arrangements are required. If samples are destroyed or misplaced, replacement samples are not readily available. In addition, if field personnel can confirm that proper dust control measures have been applied to the granular matter, then inspections and testing requirements of regulatory agencies such as the Environmental Protection Agency (EPA) and a state Department of Environmental Protection (DEP) can be waived during loading and unloading operations at shipping ports, transfer stations or production sites.

A problem associated with the TVA method mentioned above, other than the aforementioned time lag problems, is that the sample must be weighed both before and after the testing procedure. With the TVA method, granules of product may be lost during the testing procedure as a result of the open top, thus skewing the analysis to indicate higher dust readings. Losing some granules will result in a calculated higher dust content than actually exist which can result in unnecessary additional dust control agents being applied.

It is thus apparent that a need exists for a system and device which is self-contained, that is, a closed system as opposed to the open system of the device in the TVA Manual, which is easy to operate by personnel with no prior skills and minimal training needed to use the system and device, yet provides reliable dust content data for on-site assessment of dust control measures so that operators can in turn assess the effectiveness of dust control measures taken in the field.

The present invention was not obvious to those skilled in the art because on-site lab analysis is rarely done or considered in the fertilizer industry; there may be logistical problems in assembling and installing lab equipment as a permanent part of the actual production process; and prior art testing methods are sensitive to external forces such as wind or high dust in ambient air, thus impairing the effectiveness of normal testing techniques. For example, measurements taken using the TVA recommended device with its open top would be affected by surrounding winds in a high dust environment. In addition, EPA and DEP regulatory requirements have been somewhat vague regarding on-site testing requirements, thereby providing no impetus to conduct such on-site tests. Further, operators in the past have generally been more interested in qualitative information, that is, what the dust is made of, instead of quantitative information, that is, how much dust is in the fertilizer. The present invention provides a closed system which is not affected by external forces and provides valuable quantitative data from which effective dust control measures in the field can be considered.

SUMMARY OF THE INVENTION

The present invention is an apparatus and device for measuring a dust content of granules, particularly, fertilizer samples. The invention comprises an elongate vertically oriented generally cylindrical hollow tower having an intermediate portion, a bottom portion with collection means for removing the granules from the tower at a distal end of the tower, and a top portion with an air exhaust means at a proximate end of the tower, the top portion adapted to detachably engage the intermediate portion. The tower intermediate portion further includes a recirculation air inlet opening through a wall surface at a lower end of the intermediate portion, and means for introducing the granules in the tower intermediate portion, the means being located through the wall surface at an upper end of the tower intermediate portion.

The tower intermediate portion further includes inside the tower intermediate portion a plurality of horizontally oriented grates, each grate being secured in a predetermined space apart relationship between opposite ends of the tower intermediate portion.

The present invention further includes means for recirculating air through the elongate tower. The air exhaust means at the proximate end of the tower is in fluid communication with the means for recirculating air through the elongate tower, and the means for recirculating air is also in fluid communication with the recirculation air inlet opening at the lower end of the intermediate portion thereby completing a recirculation path. Also included in the invention is a filter means for filtering dust; the filter means is located inside the tower in a generally flat orientation parallel to the grates near the detachable engagement location of the intermediate portion with the top portion.

To control the flow of air through the recirculation path, the invention includes control means in the form of valves and pressure sensing means in the recirculation path on the inlet and outlet sides of the tower.

The present invention further includes a method in which the aforementioned apparatus is used in the field comprising the steps of:

(a) providing an apparatus for measuring the dust content of granules as described above;

(b) obtain and weigh a predetermined number of samples of granules, each being a predetermined weight;

(c) weigh the filter means and record the weight;

(d) activate the means for recirculating air through the tower;

(e) with the air recirculating, disengage the top portion away from the tower intermediate portion, position the filter means inside the tower in a generally flat orientation parallel to the grates near the detachable engagement location of the intermediate portion with the top portion and reposition the top portion so as to engage the intermediate portion;

(f) adjust the control means for monitoring and regulating a flow of air through the recirculation path so as to maintain a pressure of approximately 0.75 inches of water gauge pressure on the first pressure sensing means and a pressure of approximately 4.0 inches of water gauge pressure on the second pressure sensing means;

(g) slowly pour one of the predetermined number of weighed samples of granules through said means for introducing the granules;

(h) allow a predetermined amount of time for the sample of granules to settle in the bottom portion of the tower and after expiration of such time, collect the sample of granules through the collection means with a suitable container;

(i) repeat steps (g) and (h) until the sample of granules has passed through the cylindrical hollow dust tower a predetermined number of times;

(j) with the means for recirculating air activated, carefully disengage the top portion from the tower intermediate portion and remove the filter means from the tower;

(k) weigh the filter means containing a weight of dust; and (l) calculate the weight of the dust collected on the filter means by subtracting the weight of the filter means recorded in step (c) from the combined weight of the filter and dust weighed in step (k).

The above method is then repeated for each of the remaining predetermined number of samples of granules taken in step (b) above and the average weight of dust is calculated.

Thus the method of the present invention presents an easy method which requires minimal training to use the apparatus of the present invention.

BRIEF DESCRIPTION OF THE DRAWING

For a fuller understanding of the nature and objects of the invention, reference should be made to the following detailed description, taken in connection with the accompanying drawing, which is a schematic view of the present invention.

DETAILED DESCRIPTION OF THE INVENTION

Referring now to the drawing, the invention which is an apparatus for measuring a dust content of granules and is depicted generally as 10, comprises an elongate vertically oriented generally cylindrical hollow tower 12 having an intermediate portion 12a, a bottom portion 12c with collection means 32 for removing the granules 46 from the tower at a distal end of the tower 12, and a top portion 12b with an air exhaust means 34 at a proximate end of the tower 12, the top portion 12b adapted to detachably engage the intermediate portion 12a at engagement location depicted by 16 in FIG. 1.

A practical application of the collections means 32 is the providing of a compression plug or stopper made from a rubberized material, a cork material or a combination cork and rubberized material. In addition, the distal end of the tower in the bottom portion 12c may include internal or external threads wherein a threaded plug or cap may be utilized at collection means 32.

The tower intermediate portion 12a further includes a recirculation air inlet opening 28 through a wall surface at a lower end of the intermediate portion 12a, and means for introducing the granules 26 in the tower intermediate portion 12a, the means being located through the wall surface at an upper end of the tower intermediate portion 12a.

The tower intermediate portion 12a further includes inside the tower intermediate portion 12a a plurality of horizontally oriented grates 14, each grate 14 being secured in a predetermined space apart relationship, generally 3 to 6 inches apart, between opposite ends of the tower intermediate portion 12a.

The present invention also includes means for recirculating air 36 through the elongate tower 12. The air exhaust means 34 at the proximate end of the tower 12 is in fluid communication with the means for recirculating air 36 through the elongate tower 12. The means for recirculating air 36 is also in fluid communication with the recirculation air inlet opening 28 at the lower end of the intermediate portion 12a thereby completing a recirculation path.

The means for recirculating air 36 is preferably a motorized blower/vacuum combination with exhaust and vacuum connections such as is readily commercially available. However, alternative sources of air movement generating devices are possible such as pneumatic systems.

Also included is a filter means 18 for filtering dust. The filter means 18 is located inside the tower 12 in a generally flat orientation parallel to the grates 14 near the detachable engagement location 16 of the intermediate portion 12a with the top portion 12b. Filter means 18 is readily commercially available and is typically rated at 0.1 to 1.0 microns, although a practical application using 0.3 to 0.6 micron would work satisfactorily. In order for the filter means 18 to remain generally flat within the tower 12, it may be self contained in a frame and mesh combination wherein a lip or other attachment means extending from the frame and mesh combination attaches to the bottom edge of the top portion 12b; otherwise, to minimize costs, a filter such as those used in respirators may be used in combination with a horizontally oriented screen mesh 24 secured by welding, epoxy or mechanical means or other known methods of securing, inside the top portion 12b, wherein the screen mesh 24 serves to maintain or hold the generally flat filter against the screen 24 as the recirculating means 36 is operative. The screen mesh 24 is preferably made of lightweight metallic material or other similar materials used in the filtration industry and sized with a preferably ¼ inch mesh using relatively fine strands in the mesh, although a mesh size of ⅛ inch to ¾ inch size would work well.

Control means comprising first pressure sensing means 40, second pressure sensing means 38 and valves 42a,42b, 42c,42d, for monitoring and regulating a flow of air through the recirculation path is provided in the recirculation path. The direction of airflow in the recirculation path is designated by the arrows in FIG. 1.

Tower 12 is made of static-free material, preferably glass. The bottom portion 12c is preferably integral to the tower intermediate portion 12a although a mechanically sealed joint may be used. The tower intermediate portion 12a preferably includes four to six horizontally oriented grates, although three to seven grates would provide satisfactory results with five grates 14 considered the standard practice, each grate being made from any suitable material such as stainless steel, aluminum or alloy steel. Each horizontally oriented grate 14 is preferably about ½ inch mesh, although a finer or coarser mesh would work. Each grate 14 is secured in the predetermined space apart relationship with at least one vertically oriented elongate member 20 extending peripherally and generally between opposing ends of the generally cylindrical hollow tower intermediate portion 12*a*. Preferably, each grate 14 will be secured in the predetermined space apart relationship with two vertically oriented elongate members 20, each member 20 being approximately 180° apart. The members 20 are generally welded, brazed or mechanically connected to the perimeter edge of each grate 14.

In a practical application of the invention, it is preferable to provide the means 26 for introducing granules inside the tower intermediate portion 12*a* such that the entry into the intermediate portion 12*a* is at an angle of approximately 5° to 60° from a vertical outside surface of the generally cylindrical hollow tower intermediate portion 12*a*. A funnel 22 for ease in pouring the granules 46 in the tower 12 is in fluid communication with the means 26 for introducing granules inside the intermediate portion 12*a*.

Although the recirculation air inlet opening 28 through the wall surface at the lower end of the intermediate portion 12*a* may enter the tower 12 in a direction perpendicular to the outside surface of the tower 12, an alternative embodiment directs the recirculation air inlet inside the tower 12 at an angle of approximately 5° to 60° from a vertical outside surface of the tower 12.

In a preferred embodiment of the present invention, the top portion 12*b* is conically-shaped for directing air toward the air exhaust means 30 and the bottom portion 12*c* is conically-shaped for directing granules toward the collection means 32. The collection means 32 in the bottom portion 12*c* includes a removable plug or cap at the distal end of the tower 12.

The control means 36 for monitoring and regulating the flow of air through the recirculation path includes a valve 42*b* for introduction of ambient air in the recirculation path upstream of the means 36 for recirculating air, and a valve 42*a* for exhausting air from the recirculation path downstream of the means 36 for recirculating air. The valves 42*a*,42*b* may be regulating or ball valves made from any suitable material such as polyvinylchloride (PVC), stainless steel, brass, or other alloy metal valves and are typically sized from about ¾ inch to 2 inch valves, although other sizes would work well.

The control means for monitoring and regulating the flow of air through the recirculation path also includes at least one valve 42*d* in the recirculating path located between the top portion 12*b* of the tower 12 and a joint connecting the valve 42*b* for introduction of ambient air to the recirculation path. In addition, the control means for monitoring and regulating the flow of air through the recirculation path includes at least one valve 42*c* in the recirculation path located between the air recirculation air inlet opening 28 in the tower 12 and a joint connecting the valve 42*a* for exhausting air from the recirculation path. In a practical application, it is preferable that means 42*c* and 42*d* comprise two valves respectively, one being a ball valve for immediate isolation of the tower 12 and the other being a gate valve or needle-type valve or other similar functioning valve for regulating the airflow velocity through the recirculation path.

The control means for monitoring and regulating the flow of air through the recirculation path further includes a first pressure sensing means 40 for visibly monitoring the pressure in the recirculation path at a location proximate the recirculation air inlet opening 28 in the tower 12 and a second pressure sensing means 38 for visibly monitoring the pressure in the recirculation at a location proximate the air exhaust means 30 in the top portion 12. A manometer or Bourdon-tube gauge is recommended for each pressure sensing means 40,38.

The recirculation path includes vibration dampening portions 34 in the form of flexible hoses or couplings proximate the air exhaust means 30 in the top portion 12*b* and the recirculation air inlet opening 28 in the tower 12. The recirculation path can be constructed from many of several known methods in the art, to include PVC piping or tubing, metallic piping or tubing, PVC or rubberized hoses, or combinations thereof, among others. It is recommended, although not necessarily required, that a vibration dampening features be added to separate the glass tower from the remainder of the recirculation path to minimize the chance of glass breakage at the tower points of entry and exit, 28 and 30 respectively. For costs savings, it is recommended that a combination PVC rigid piping be used for the valve components and air recirculation means 36 together with short segments of flexible hoses or flexible couplings attached to the tower 12 at 28 and 30. The flexible hoses can be made from a flexible rubberized material or from a PVC flexible thin wall material. Rigid pipe material can be made from schedule 40 piping or thinner walled tubing readily available in the commercial markets. If PVC material is used, joints can be readily cemented together, although threaded or union connections are acceptable. It is also recommended that the piping and vibration dampening feature 34 at air exhaust means 30 be arranged such that a slight compressive force is created between the tower intermediate portion 12*a* and the top portion 12*b* so that the integrity of engagement location 16 can be maintained while the recirculation means 36 is operative.

In a practical application of the present invention, a housing 44, shown in phantom in FIG. 1, may be used to enclose the air recirculation means 36. The housing 44 can then be used to attach various components of the invention to an outside surface of one of its side 44*b*. For example, the tower intermediate portion 12*a* can be detachably secured to a side 44*b*, along with the gauges 38,40 and segments of any of the recirculation path piping, including any valves. The housing 44 has four integral sides 44*b*, a bottom 44*c* integral to the sides 44*b*, and a removable top cover 44*a*. The housing further includes apertures at predetermined locations in any one of the sides for running conduit comprising the recirculation path between the tower 12 and the means for recirculating air 36. The housing 44 can be made of light-weight aluminum or with wooden laminate structure such as plywood with a Formica laminate. A practical adaptation of the housing 44 is the inclusion of weatherproof electrical box connections incorporating a power source connection to provide power to the air recirculation means 36, a remote on/off switch for the air recirculation means 36 within the housing and receptacles for powering accessories such as lights.

Also presented herein is a method of using the apparatus 10 described above comprising the steps of:
  (a) providing an apparatus 10 for measuring the dust content of granules 46 comprising a static-free elongate vertically oriented generally cylindrical hollow tower 12 having an intermediate portion 12*a*, a bottom portion 12*c* with collection means 32 for removing the granules 46 from the tower 12 at a distal end of the tower 12, and a top portion 12b with an air exhaust means 30 at a proximate end of the tower 12, the top portion 12b adapted to detachably engage the intermediate portion 12a, the tower intermediate portion 12a further including a recirculation air inlet opening 28 through a wall surface at a lower end of the intermediate portion 12a, and means 26 for introducing the granules 46 in the tower intermediate portion 12a, the means 26 being located through the wall surface at an upper end of the tower intermediate portion 12a, the tower intermediate portion 12a further including inside the tower intermediate portion 12a a plurality of horizontally oriented grates 14, each grate 14 being secured in a predetermined space apart relationship between opposite ends of the tower intermediate portion 12a, means for recirculating air through the elongate tower 12, the air exhaust means 30 at the proximate end of the tower 12 being in fluid communication with the means for recirculating air 36 through the elongate tower 12, the means for recirculating air 36 further being in fluid communication with the recirculation air inlet opening 28 at the lower end of the intermediate portion 12a thereby completing a recirculation path, filter means 18 for filtering dust, control means for monitoring and regulating a flow of air through the recirculation path, the control means for monitoring and regulating the flow of air through the recirculation path includes a valve 42b for introduction of ambient air in the recirculation path upstream of the means for recirculating air 36, and a valve 42a for exhausting air from the recirculation path downstream of the means for recirculating air 36, the control means including a first pressure sensing means 40 for visibly monitoring the pressure in the recirculation path at a location proximate the recirculation air inlet opening 28 in the tower and a second pressure sensing means 38 for visibly monitoring the pressure in the recirculation path at a location proximate the air exhaust means 30 in the top portion 12b, the control means further including at least one valve 42d in the recirculation path located between the top portion 12b of the tower 12 and a joint connecting the valve 42b for introduction of ambient air to the recirculation path, the control means further including at least one valve 42c in the recirculation path located between the air recirculation air inlet opening 28 in the tower 12 and a joint connecting the valve 42a for exhausting air from the recirculation path.

(b) obtain and weigh a predetermined number of samples of granules 46, each being a predetermined weight (it is preferable that two to four samples of granules 46, each weighing 200 grams will provide satisfactory results, with three samples being an acceptable standard practice);

(c) weigh the filter means 18 and record the weight;

(d) activate the means for recirculating air 36 through the tower 12;

(e) with the air recirculating, disengage the top portion 12b from the tower intermediate portion 12a, position the filter means 18 inside the tower 12 in a generally flat orientation parallel to the grates 14 near the detachable engagement location 16 of the intermediate portion 12a with the top portion 12b and reposition the top portion 12b so as to engage the intermediate portion 12a;

(f) adjust the control means 42(a,b,c,d) for monitoring and regulating a flow of air through the recirculation path so as to maintain a pressure of approximately 0.75 inches of water gauge pressure on the first pressure sensing means 40 and a pressure of approximately 4.0 inches of water gauge pressure on the second pressure sensing means 38;

(g) slowly pour one of the predetermined number of weighed samples of granules 46 through said means 26 for introducing the granules 46;

(h) after the sample of granules 46 settles in the bottom portion 12c of the tower 12, collect the sample of granules 46 through the collection means 32 with a suitable container 48 (shown in phantom in FIG. 1);

(i) repeat steps (g) and (h) until the sample of granules 46 has passed through the cylindrical hollow dust tower 12 a predetermined number of times, preferably 6 times, although 1 to 10 times will provide data with which dust control evaluations can be made;

(j) with the means for recirculating air 36 activated, carefully disengage the top portion 12b from the tower intermediate portion 12a and remove the filter means 18 from the tower 12;

(k) weigh the filter means 18 containing a weight of dust; and (l) calculate the weight of the dust collected on the filter means 18 by subtracting the weight of the filter means 18 recorded in step (c) from the combined weight of the filter means 18 and dust weighed in step (k).

Depending on the filter medium used, some filters have powder or loose fibrous material that may be displaced from the filter when air is blown through the filter; therefore requiring minor adjustments to the calculations or preconditioning the filters to blow off such loose powder or fibers. For example, if a filter is placed in the present invention and the air recirculation means 36 is turned on with no granules being poured into the tower 12, a weighing of the filter before and after the air recirculation means 36 is turned on may show an approximate difference of 0.015 grams in weight. Should this type of filter be used, then the weight of the dust collected in step (1) above must be increased by 0.015 grams. Of course, higher quality filters may make this adjustment unnecessary or a user may simply precondition the filters before use by blowing air through the them thereby making the adjustment unnecessary.

The above method is then repeated for each of the remaining predetermined number of samples of granules 46 taken in step (b) above and the average weight of dust is then calculated.

A practical example of calculating the percentage of dust and converting the percent to pounds of dust per ton utilizes the following formula:

$$\text{pounds per ton} = \frac{(\text{average weight of dust} \times 100) \times 20}{200 \text{ grams}}$$

As seen from the foregoing description, the present invention satisfies a long felt need to provide an apparatus which can be transported to the field to provide means for effective on-site testing for the levels of dust in fertilizer, thereby providing valuable cost savings in the fertilizer processing industries.

The invention is clearly new and useful. Moreover, it was not obvious to those of ordinary skill in this art at the time it was made, in view of the prior art considered as a whole as required by law.

It will thus be seen that the objects set forth above, and those made apparent from the foregoing description, are efficiently attained and since certain changes may be made in the above construction without departing from the scope of the invention, it is intended that all matters contained in the foregoing construction or shown in the accompanying drawings shall be interpreted as illustrative and not in the limiting sense.

It is also to be understood that the following claims are intended to cover all of the generic and specific features of the invention herein described, and all statements of the scope of the invention which, as a matter of language, might be said to fall therebetween.

Now that the invention has been described.

What is claimed is:

1. An apparatus for measuring a dust content of granules comprising:

an elongate vertically oriented generally cylindrical hollow tower having an intermediate portion, a bottom portion with collection means for removing the granules from the tower at a distal end of the tower, and a top portion with an air exhaust means at a proximate end of the tower, the top portion adapted to detachably engage the intermediate portion;

the tower intermediate portion further including a recirculation air inlet opening through a wall surface at a lower end of the intermediate portion, and means for introducing the granules in the tower intermediate portion, the means being located through the wall surface at an upper end of the tower intermediate portion;

the tower intermediate portion further including inside the tower intermediate portion a plurality of horizontally oriented grates, each grate being secured in a predetermined space apart relationship between opposite ends of the tower intermediate portion;

means for recirculating air through the elongate tower;

the air exhaust means at the proximate end of the tower being in fluid communication with the means for recirculating air through the elongate tower, the means for recirculating air further being in fluid communication with the recirculation air inlet opening at the lower end of the intermediate portion thereby completing a recirculation path;

filter means for filtering dust, the filter means being located inside the tower in a generally flat orientation parallel to the grates near the detachable engagement location of the intermediate portion with the top portion; and control means for monitoring and regulating a flow of air through the recirculation path.

2. An apparatus for measuring a dust content of granules according to claim 1 wherein the tower is made of static-free material.

3. An apparatus for measuring a dust content of granules according to claim 2 wherein the static-free material is glass.

4. An apparatus for measuring a dust content of granules according to claim 1 wherein the plurality of horizontally oriented grates is three to seven.

5. An apparatus for measuring a dust content of granules according to claim 1 wherein each horizontally oriented grate is about ½ inch mesh.

6. An apparatus for measuring a dust content of granules according to claim 1 wherein each grate is secured in the predetermined space apart relationship with at least one vertically oriented elongate member extending peripherally and generally between opposing ends of said generally cylindrical hollow tower intermediate portion.

7. An apparatus for measuring a dust content of granules according to claim 6 wherein each grate is secured in the predetermined space apart relationship with two vertically oriented elongate members, each being approximately 180° apart.

8. An apparatus for measuring a dust content of granules according to claim 1 wherein the means for introducing granules is directed inside the tower intermediate portion at an angle of approximately 5° to 60° from a vertical outside surface of said generally cylindrical hollow tower intermediate portion.

9. An apparatus for measuring a dust content of granules according to claim 8 wherein the means for introducing granules includes a funnel for ease in pouring the granules in the tower.

10. An apparatus for measuring a dust content of granules according to claim 1 wherein the recirculation air inlet opening through the wall surface at the lower end of the intermediate portion is directed inside said elongate tower at an angle of approximately 5° to 60° from a vertical outside surface of the tower.

11. An apparatus for measuring a dust content of granules according to claim 1 wherein the filter means for filtering dust is rated at 0.1 to 1.0 microns.

12. An apparatus for measuring a dust content of granules according to claim 1 wherein the filter means includes a horizontally oriented screen mesh secured inside the top portion and a generally flat dust filter, the screen mesh for holding the generally flat filter against the screen when the means for recirculating air is operative.

13. An apparatus for measuring a dust content of granules according to claim 1 wherein the top portion is conically-shaped for directing air toward the air exhaust means.

14. An apparatus for measuring a dust content of granules according to claim 1 wherein the bottom portion is conically-shaped for directing granules toward the collection means.

15. An apparatus for measuring a dust content of granules according to claim 1 wherein the collection means in the bottom portion includes a removable plug or cap at the distal end of the tower.

16. An apparatus for measuring a dust content of granules according to claim 1 wherein the control means for monitoring and regulating the flow of air through the recirculation path includes a valve for introduction of ambient air in the recirculation path upstream of the means for recirculating air, and a valve for exhausting air from the recirculation path downstream of the means for recirculating air.

17. An apparatus for measuring a dust content of granules according to claim 16 wherein the control means for monitoring and regulating the flow of air through the recirculation path includes at least one valve in the recirculating path located between the top portion of the tower and a joint connecting the valve for introduction of ambient air to the recirculation path.

18. An apparatus for measuring a dust content of granules according to claim 16 wherein the control means for monitoring and regulating the flow of air through the recirculation path includes at least one valve in the recirculation path located between the air recirculation air inlet opening in the tower and a joint connecting the valve for exhausting air from the recirculation path.

19. An apparatus for measuring a dust content of granules according to claim 1 wherein the control means for monitoring and regulating the flow of air through the recirculation path includes a first pressure sensing means for visibly monitoring the pressure in the recirculation path at a location proximate the recirculation air inlet opening in the tower and a second pressure sensing means for visibly monitoring the pressure in the recirculation at a location proximate the air exhaust means in the top portion.

20. An apparatus for measuring a dust content of granules according to claim 1 wherein the recirculation path includes vibration dampening portions in the form of flexible hoses or couplings proximate the air exhaust means in the top portion and the recirculation air inlet opening in the tower.

21. An apparatus for measuring a dust content of granules according to claim 1 wherein the bottom portion is integral to the intermediate portion.

22. An apparatus for measuring a dust content of granules according to claim 19 further comprising:

a housing for housing the means for recirculating air;

the housing having four integral sides, a bottom integral to the sides, and a removable top cover;

the housing further including apertures at predetermined locations in any one of the sides for running conduit comprising the recirculation path between the tower and the means for recirculating air;

the tower being detachably secured to an outside surface of the side of the housing; and the first and second pressure sensing means are secured to an outside surface of the side of the housing.

23. An apparatus for measuring a dust content of granules according to claim 12 wherein the screen mesh is sized from an approximate 1/8 inch mesh to an approximate 3/4 inch mesh.

24. A method for measuring a dust content of granules comprising the steps of:

(a) providing an apparatus for measuring the dust content of granules comprising a static-free elongate vertically oriented generally cylindrical hollow tower having an intermediate portion, a bottom portion with collection means for removing the granules from the tower at a distal end of the tower, and a top portion with an air exhaust means at a proximate end of the tower, the top portion adapted to detachably engage the intermediate portion, the tower intermediate portion further including a recirculation air inlet opening through a wall surface at a lower end of the intermediate portion, and means for introducing the granules in the tower intermediate portion, the means being located through the wall surface at an upper end of the tower intermediate portion, the tower intermediate portion further including inside the tower intermediate portion a plurality of horizontally oriented grates, each grate being secured in a predetermined space apart relationship between opposite ends of the tower intermediate portion, means for recirculating air through the elongate tower, the air exhaust means at the proximate end of the tower being in fluid communication with the means for recirculating air through the elongate tower, the means for recirculating air further being in fluid communication with the recirculation air inlet opening at the lower end of the intermediate portion thereby completing a recirculation path, filter means for filtering dust, control means for monitoring and regulating a flow of air through the recirculation path, the control means for monitoring and regulating the flow of air through the recirculation path includes a valve for introduction of ambient air in the recirculation path upstream of the means for recirculating air, and a valve for exhausting air from the recirculation path downstream of the means for recirculating air, the control means including a first pressure sensing means for visibly monitoring the pressure in the recirculation path at a location proximate the recirculation air inlet opening in the tower and a second pressure sensing means for visibly monitoring the pressure in the recirculation path at a location proximate the air exhaust means in the top portion, the control means further including at least one valve in the recirculating path located between the top portion of the tower and a joint connecting the valve for introduction of ambient air to the recirculation path, the control means further including at least one valve in the recirculation path located between the air recirculation air inlet opening in the tower and a joint connecting the valve for exhausting air to the recirculation path;

(b) obtain and weigh a predetermined number of samples of granules, each being a predetermined weight;

(c) weigh the filter means and record the weight;

(d) activate the means for recirculating air through the tower;

(e) with the air recirculating, disengage the top portion from the tower intermediate portion, position the filter means inside the tower in a generally flat orientation parallel to the grates near the detachable engagement location of the intermediate portion with the top portion and reposition the top portion so as to engage the intermediate portion;

(f) adjust the control means for monitoring and regulating a flow of air through the recirculation path so as to maintain a pressure of approximately 0.75 inches of water gauge pressure on the first pressure sensing means and a pressure of approximately 4.0 inches of water gauge pressure on the second pressure sensing means;

(g) slowly pour one of the predetermined number of weighed sample of granules through said means for introducing the granules;

(h) after the sample of granules settles in the bottom portion of the tower, collect the sample of granules through the collection means with a suitable container;

(i) repeat steps (g) and (h) until the sample of granules has passed through the cylindrical hollow dust tower a predetermined number of times;

(j) with the means for recirculating air activated, carefully disengage the top portion from the intermediate portion and remove the filter means from the tower;

(k) weigh the filter means containing a weight of dust; and (l) calculate the weight of the dust collected on the filter by subtracting the weight of the filter means recorded in step (c) from the combined weight of the filter and dust weighed in step (k).

25. The method according to claim 24 further comprising the step of repeating steps (c)–(l) for each of the remaining predetermined number of samples of granules taken in step (b) and averaging the calculated weights.

* * * * *